United States Patent [19]

Clark et al.

[11] Patent Number: 5,032,395
[45] Date of Patent: Jul. 16, 1991

[54] METHOD OF INDUCING LEUKOCYTOSIS WITH A COMBINATION OF IL-3 AND GM-CSF

[75] Inventors: Steven C. Clark, Winchester; Agnes B. Ciarletta, Haverhill; Yu-Chung Yang, Arlington; Robert E. Donahue, Shirley, all of Mass.

[73] Assignee: Genetics Institute, Inc., Cambridge, Mass.

[21] Appl. No.: 370,680

[22] Filed: Jun. 23, 1989

Related U.S. Application Data

[63] Continuation-in-part of Ser. No. 107,613, Oct. 9, 1987, abandoned, which is a continuation-in-part of Ser. No. 916,335, Oct. 7, 1986, Pat. No. 4,877,729, which is a continuation-in-part of Ser. No. 885,060, Jul. 14, 1986, abandoned.

[51] Int. Cl.⁵ ............................................ A61K 37/02
[52] U.S. Cl. .................................... 424/85.1; 424/85.2; 514/2; 514/8; 514/12; 514/21
[58] Field of Search ........................... 514/2, 8, 24, 12; 424/85.1, 85.2

[56] References Cited

PUBLICATIONS

Quesenberry et al., *Blood*, 65, 1985, pp. 214–217.
Bartelmez et al., *J. Cell. Physiol.* 122, 1985, pp. 370–378.
Old, *Nature*, 1987, pp. 330–331, vol. 326.
Yokota et al., *Bioessays*, vol. 5(4), 1986, pp. 166–171.
Dexter et al., *Bioessays*, vol. 2(4), 1985, pp. 154–158.
Koike, *Blood*, 75:2286 (1990).

*Primary Examiner*—Garnette D. Draper
*Attorney, Agent, or Firm*—Luann Cserr; Bruce Eisen

[57] ABSTRACT

An improved method for inducing leukocytosis in a primate is disclosed. The method includes co-administering IL-3 in conjunction with GM-CSF, such that the leukocyte count in the primate is synergistically raised.

2 Claims, 2 Drawing Sheets

METHOD OF INDUCING LEUKOCYTOSIS WITH A COMBINATION OF IL-3 AND GM-CSF

This is a continuation-in-part of pending U.S. Pat. application Ser. No. 107,613 filed October 9, 1987,, which is a continuation-in-part of U.S. Pat. application Ser. No. 916,335 filed Oct. 7, 1986,which is a continuation-in-part of U. S. Pat. application Ser. No. 885,060 filed July 14, 1986, now abandoned.

Hematopoietic growth factors are hormone like proteins that induce the growth and differentiation of mature blood cells from undifferentiated stem cells. Various classes of growth factors, having different inductive capabilities, have been discovered. In particular, GM-CSF exhibits a stimulatory effect on the development of neutrophilic granulocytes, macrophages, and eosinophils, which develop later in the ontogenic process after cells have become committed to a single line of development.

Because of its stimulatory effects on hematopoiesis, considerable interest has developed in GM-CSF as a therapeutic agent. Therapeutic utilities for GM-CSF include treatment of myelosuppression, a common and serious complication of chemotherapy or irradiation treatment and the acceleration of hematopoietic recovery after autol ogous bone marrow transplantation. However, trials of GM-CSF in patients with inoperable sarcoma, breast cancer or melanoma undergoing intensive chemotherapy indicate that GM-CSF's ability to stimulate leukocytosis is limited by certain toxic side effects observed at higher dosage levels: myalgias, fluid retention, pericardial and pleural effusion, thrombus formation and pulmonary emboli. See K.S. Antman, N. Eng. J. Med. 319:593-98 (1988); S.J. Brandt, N. Enq. J. Med. 318:869-76 (1988).

We have surprisingly discovered that the leukocytic activity of GM-CSF can be substantially enhanced by co-administering interleukin-3 (IL-3), in particular, by the administration of IL-3 prior to the administration of GM-CSF. IL-3 is a growth factor that exhibits a stimulatory effect on the proliferation of relatively early stem cells, leading to the development of cells which are then committed to erythroid, lymphoid and myeloid lineages. When even very low doses of GM-CSF are co-administered with IL-3 to primates in accordance with the method of this invention, a dramatic leukocytosis is elicited, far greater than that achieved with IL-3 alone or with GM-CSF alone. GM-CSF's potential as a therapeutic agent is substantially enhanced by the method of the invention, because at low doses, the toxic side effects discussed above may be substantially avoided.

All biologically active forms of IL-3 and GM-CSF are useful in the method of the present invention. As used herein, IL-3 and GM-CSF refer collectively to both native and recombinant forms of IL-3 and GM-CSF. The terms likewise comprehend alleles, muteins, derivatives (e.g. PEGylated IL-3) and analogues of the natural and recombinant proteins which may contain amino acid deletions, substitutions and/or insertions but which possess biological activity characteristic of IL-3 or GM-CSF.

IL-3 and its production by recombinant DNA technology is described in Yang, et al., *Cell* 47:3-10 (1986), and WO 88/00598 published on Jan. 28, 1988.

GM-CSF can be produced as described in Wong, et al., *Cancer cells* 3/Growth Factors and Transformation, pps 235-242 (1985); *Prog. Clin. Biol. Res.* 191:351-366 (1985); *Science* 228:810-815 (1985) and in WO 86/00639 published on Jan. 30, 1986.

In practicing the method of this invention, first IL-3 and then GM-CSF are administered to a primate requiring raising of its leukocyte count. This schedule of administration causes a synergistic rise in the leucocyte count. By synergistic rise, we mean a resulting leukocyte count greater than the leukocyte count resulting from administration of the same amount of IL-3 alone or the same amount of GM-CSF alone.

Generally, the amount of IL-3 will range from 0.5 to 50 micrograms per kg body weight and the amount of GM-CSF will range from 0.5 to 100 micrograms. Generally, the IL-3 is administered for 7 days and the GM-CSF is administered subsequent to the IL-3, for 1 to 21 days.

Administration of IL-3 and GM-CSF can be carried out in a variety of conventional ways. Parenteral administration is preferred; either by subcutaneous, intramuscular or intravenous injection. In either case, the IL-3 and GM-CSF will be in form pyrogen-free, parenterally acceptable aqueous solutions. The preparation of such parenterally acceptable protein solutions, having due regard to pH, isotonicity, stability and the like, is within the skill of the art.

The improved method of the present invention may be used in the treatment of diseases characterized by a decreased level of cells of the hematopoietic system, for example leukopenia, or in the treatment of various immunodeficiencies resulting from viral or retroviral infection, severe exposure to radiation, or cancer therapy. Co-administration of IL-3 and GM-CSF may also be employed in the treatment of other blood cell deficiencies, for example thrombocytopenia (platelet deficiency) and anemia (red cell deficiency).

The following examples illustrate the method of the present invention.

EXAMPLE I

Figure 1:
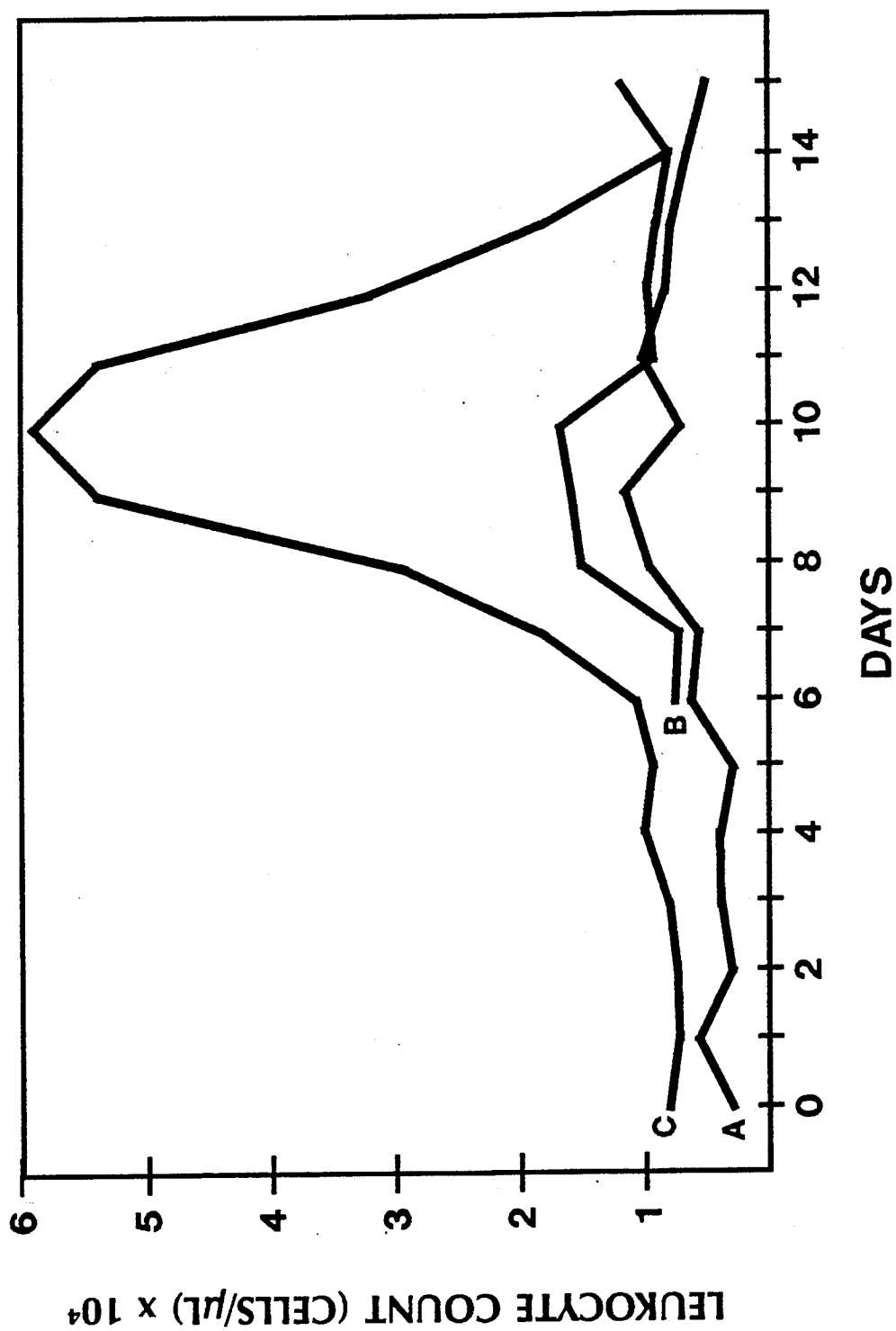
FIG. 1 is a graphic representation comparing the effects of IL-3 administration, GM-CSF administration and IL-3, GM-CSF co-administration on a primate in accordance with Example I.
Figure 2:
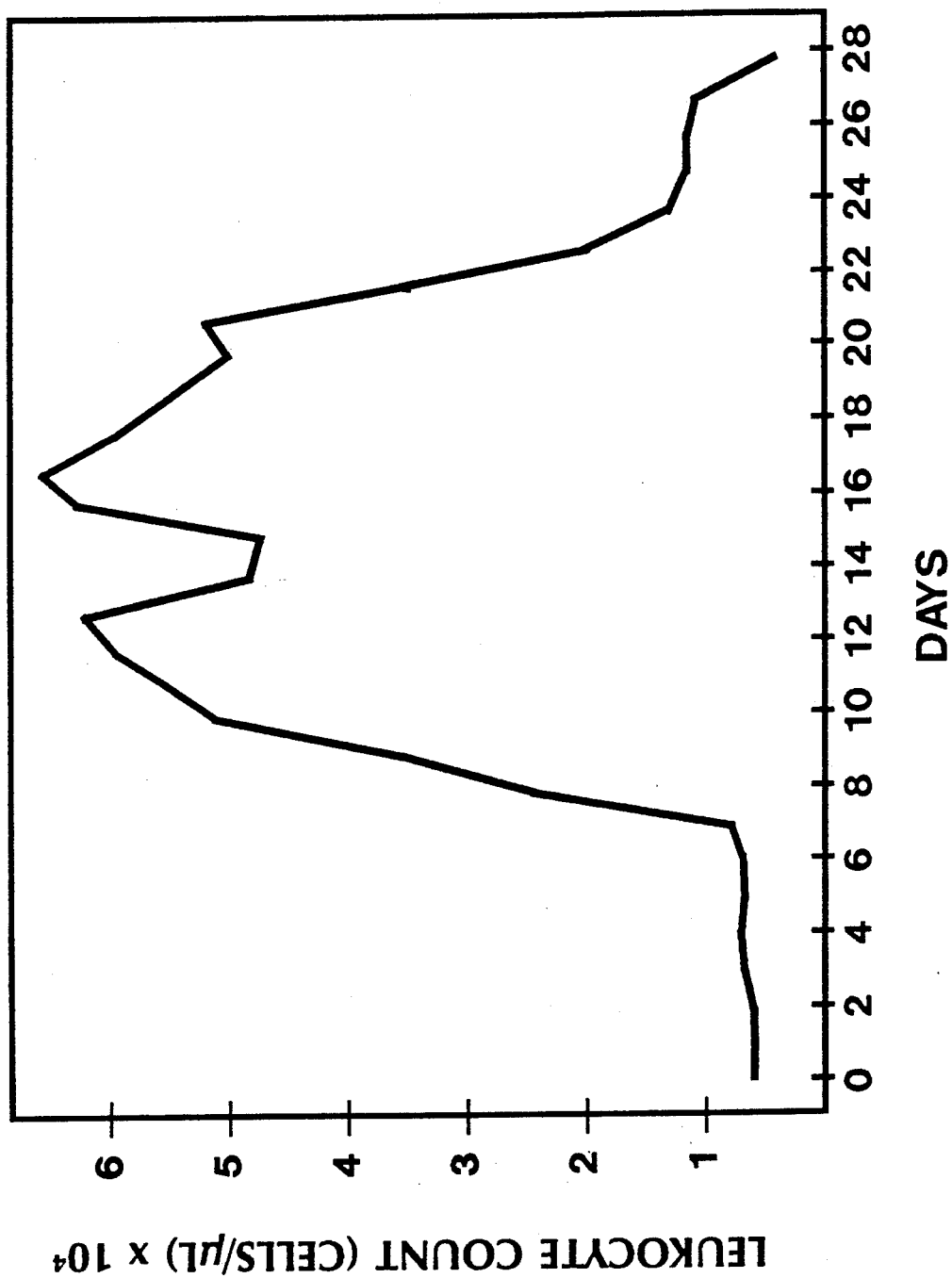
FIG. 2 is a graphic representation of the results of the test of IL-3-induced enhancement set forth in Example II.

In this experiment, the same cynomolgus macaque (*Macaca fasicularis*) was administered by continuous intravenous infusion (A) IL-3 alone at the rate of 20 $\mu$g kg$^{-1}$ day$^{-1}$ for 7 days; (B) GM-CSF alone at the rate of 20 $\mu$g kg$^{-1}$ day$^{-1}$ for 4 days; or (C) IL-3 at the rate of 20 $\mu$g kg$^{-1}$ day$^{-1}$ on days 1 through 7 followed by GM-CSF at the rate of 2 $\mu$g kg$^{-1}$ day-1 on days 7 through 10. The animal was rested for at least 14 days between each set of infusions. The differential cell counts were performed on daily blood samples. The counts include eosinophil, monocyte, lymphocyte, band basophil and neutrophil levels.

EXAMPLE II

To test the duration of the IL-3-induced enhancement, one healthy cynomolgus macaque was continuously infused GM-CSF at the rate of 2 $\mu$g kg$^{-1}$ day-1 for 14 days after a 7 day treatment with IL-3 at the rate of 20 $\mu$g kg$^{-1}$ day$^{-1}$ The leukocytosis observed was maintained at about 45,000 cells per microliter or above for the duration of the GM-CSF administration, demonstrating that the treatment with IL-3 primed the hematopoietic system to respond to GM-CSF for at least 14 days.

We claim:

1. A method for inducing leukocytosis in a primate comprising co-administering IL-3 and GM-CSF to said primate, such that the leukocyte count in said primate is synergistically raised.

2. A method according to claim 1 wherein said IL-3 is administered prior to administration of said GM-CSF.